US012110271B2

(12) United States Patent
Shin et al.

(10) Patent No.: US 12,110,271 B2
(45) Date of Patent: Oct. 8, 2024

(54) MANUFACTURING METHOD FOR 4-METHOXYPYRROLE DERIVATIVES

(71) Applicant: Daewoong Pharmaceutical Co., Ltd., Gyeonggi-do (KR)

(72) Inventors: Jeong-Taek Shin, Gyeonggi-do (KR); Jeong-Hyun Son, Gyeonggi-do (KR); Deok Ki Eom, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 849 days.

(21) Appl. No.: 17/273,390

(22) PCT Filed: Sep. 19, 2019

(86) PCT No.: PCT/KR2019/012122
§ 371 (c)(1),
(2) Date: Mar. 4, 2021

(87) PCT Pub. No.: WO2020/060213
PCT Pub. Date: Mar. 26, 2020

(65) Prior Publication Data
US 2021/0221770 A1    Jul. 22, 2021

(30) Foreign Application Priority Data

Sep. 19, 2018  (KR) .................. 10-2018-0112196
Sep. 6, 2019   (KR) .................. 10-2019-0110997

(51) Int. Cl.
C07D 207/48    (2006.01)

(52) U.S. Cl.
CPC .................... *C07D 207/48* (2013.01)

(58) Field of Classification Search
None
See application file for complete search history.

(56) References Cited

U.S. PATENT DOCUMENTS

| | | | |
|---|---|---|---|
| 4,194,003 A | 3/1980 | Laforest et al. | |
| 8,048,909 B2 | 11/2011 | Kajino et al. | |
| 8,338,461 B2 | 12/2012 | Kajino et al. | |
| 9,499,483 B2 | 11/2016 | Watanabe et al. | |
| 10,100,010 B1 | 10/2018 | Lee et al. | |
| 10,308,605 B2 | 6/2019 | Kajino et al. | |
| 10,336,695 B2 | 7/2019 | Kim et al. | |
| 10,487,053 B2 | 11/2019 | Kim et al. | |
| 10,683,268 B2 | 6/2020 | Kim et al. | |
| 10,710,961 B2 | 7/2020 | Shin et al. | |
| 10,889,545 B2 | 1/2021 | Kim et al. | |
| 10,913,715 B2 | 2/2021 | Kim et al. | |
| 2008/0139639 A1 | 6/2008 | Kajino et al. | |
| 2010/0216748 A1 | 8/2010 | Faghih et al. | |
| 2011/0059940 A1 | 3/2011 | Gilligan | |
| 2011/0288040 A1 | 11/2011 | Hasuoka et al. | |
| 2015/0307449 A1 | 10/2015 | Lan et al. | |
| 2019/0047953 A1 | 2/2019 | Kim et al. | |
| 2020/0181080 A1 | 6/2020 | Shin et al. | |
| 2021/0139424 A1 | 5/2021 | Kim et al. | |
| 2021/0221770 A1 | 7/2021 | Shin et al. | |

FOREIGN PATENT DOCUMENTS

| | | |
|---|---|---|
| AU | 2019343857 B2 | 12/2021 |
| CA | 2446820 A1 | 11/2002 |
| CN | 104447491 A | 3/2015 |
| CN | 106432191 A | 2/2017 |
| CN | 107001263 A | 8/2017 |
| CN | 107879964 A | 4/2018 |
| CN | 108503621 A | 9/2018 |
| CO | 2019012686 A2 | 4/2020 |
| EA | 29788 | 5/2018 |
| EP | 001534 A1 | 4/1979 |
| EP | 1803709 A1 | 7/2007 |
| EP | 2358700 A1 | 8/2011 |
| EP | 3854784 A1 | 7/2021 |
| KR | 10-2007-0060133 | 6/2007 |
| KR | 10-2015-0084974 A | 7/2015 |
| KR | 10-1613245 B1 | 4/2016 |
| RU | 2415838 C2 | 4/2011 |
| WO | WO-02/094833 A1 | 11/2002 |
| WO | WO-2004/026828 A1 | 4/2004 |
| WO | WO-2008/108380 A2 | 9/2008 |
| WO | WO-2010/013823 A2 | 2/2010 |
| WO | WO-2010/024451 A1 | 3/2010 |
| WO | WO-2010038948 A2 | 4/2010 |
| WO | WO-2010/069879 A1 | 6/2010 |
| WO | WO-2015/129755 A1 | 9/2015 |
| WO | WO-2016175555 A1 | 11/2016 |
| WO | WO-2017/164576 A1 | 9/2017 |
| WO | WO-2017164575 A1 | 9/2017 |

(Continued)

OTHER PUBLICATIONS

Feliciano, A. S., et al., "Pyrrole Derivatives from a-Ketoaldehydes", 45 Tetrahedron, pp. 6553-6562 (1989).
Groselj, U., et al., "a-Amino Acid Derived Enaminones and Their Application in the Synthesis of N-protected Methyl 5-substituted-4-hydroxypyrrole-3-carboxylates and Other Heterocycles", Tetrahedron, vol. 69, pp. 11092-11108 (2013).
Gupta, S., et al., "New Reactions and Reagents, IV. A New Synthesis of Pyrroles from x-Amino Acids", Synthesis, 726-727 (1975).
Khalili, B., et al., "Novel One-Pot, Three Component Synthesis of New 2-Alkyl-5-aryl-(lH)-pyrrole-4-ol in Water", Journal of Organic Chemistry, 73, pp. 2090-2095 (2008).
Office Action in Colombian Applicatioon No. NC2021/0003195 dated Jul. 11, 2023, 8 pages.
Yadav, R., et al., "Meridianin derivatives as potent Dyrk1A inhibitors and neuroprotective agents", Bioorganic & Medicinal Chemistry Letters, vol. 25, No. 15, pp. 1-5 (2015).
Yamakawa, T., et al., "A New Reduction of Some Carboxylic Esters with Sodium Borohydride and Zinc Chloride in the Presence of a Tertiary Amine", Bulletin of the Chemical Society of Japan, 64(9), pp. 2730-2734 (1991).

(Continued)

*Primary Examiner* — Zinna Northington Davis
(74) *Attorney, Agent, or Firm* — MARSHALL, GERSTEIN & BORUN LLP

(57) ABSTRACT

The present disclosure relates to a manufacturing method for 4-methoxypyrrole derivatives. The embodiment of the present disclosure is useful for industrial mass production of 4-methoxypyrrole derivatives, because the process efficiency and yield are improved, and the use of hazardous reagents and environmental polluting reagents is avoided.

22 Claims, No Drawings

(56) References Cited

FOREIGN PATENT DOCUMENTS

| WO | WO-2018/221971 A1 | 12/2018 |
| WO | WO-2018/236153 A1 | 12/2018 |
| WO | WO-2020/060213 A1 | 3/2020 |
| WO | WO-2022/250472 A1 | 12/2022 |

OTHER PUBLICATIONS

De Mico et al., "A Versatile and Highly Selective Hypervalent Iodine (III)/2,2,6,6-Tetramethyl-1-piperidinyloxyl-Mediated Oxidation of Alcohols to Carbonyl Compounds", J. Org. Chem, vol. 62, 1997, pp. 6974-6977.

Still et al., "Rapid Chromatographic Technique for Preparative Separations With Moderate Resolution", J. Org. Chem, vol. 43, No. 14, 1978, pp. 2923-2925.

Ranu et al., "Use of Zinc Borohydride for Efficient Reduction of Carboxylic Ester to Alcohol. Selective Reduction of Aliphatic Ester in Presence of Aromatic Ester Under Sonication", Tetrahedron Letters, vol. 32, No. 27, 1991, pp. 3243-3246.

Gallant et al., "Discovery of MK-7246, a Selective CRTH2 Antagonist for the Treatment of Respiratory Diseases", Bioorganic & Medicinal Chemistry Letters 21, 2011, pp. 288-293.

Search Report in International Application No. PCT/KR2019/012122 Jan. 2, 2020, 8 pages.

Ricko, S., et al., "Organocatalyzed Deracemization of Δ2-Pyrrolin-4-ones", Advanced Synthesis & Catalvsis, vol. 359, pp. 2288-2296 (2017).

Notice of Opposition of Ecuador Patent Application No. 2021-19076, Proceeding No. SENADI-202-19076 (with English translation of the substantive notice) (73 pages) (2022).

Office Action in CA Application No. 3,110,830 dated Sep. 5, 2023, 3 pages.

MANUFACTURING METHOD FOR 4-METHOXYPYRROLE DERIVATIVES

TECHNICAL FIELD

The present disclosure relates to a manufacturing method for 4-methoxypyrrole derivatives.

BACKGROUND OF ART

Gastrointestinal track ulcers, gastritis, and reflux esophagitis occur while the balance between aggressive factors (e.g., gastric acid, *Helicobacter pylori* pepsin, stress, alcohol, tobacco, etc.) and protective factors (e.g., gastric mucosa, bicarbonate, prostaglandins, the degree of blood supply, etc.) is destroyed. Therefore, a therapeutic agent for gastrointestinal damage such as gastrointestinal track ulcers, gastritis and reflux esophagitis is divided into a drug for inhibiting the aggressive factors and a drug for enhancing the protective factors.

Meanwhile, it is reported that gastrointestinal track ulcers, gastritis and reflux esophagitis cause ulcers even without an increase in secretion of gastric acid. Thus, as much as the aggressive factor increases, a reduction in protective factors due to a pathological change of the gastric mucosa is thought to play an important role in the occurrence of gastric ulcers. Therefore, in addition to drugs for inhibiting the aggressive factor, drugs for enhancing the protective factors are used for the treatment of gastrointestinal ulcers and gastritis. As the drugs for enhancing protective factors, mucosal protective drugs which are attached to the ulcer site to form a physicochemical membrane and drugs that promote the synthesis and secretion of mucus have been known.

On the other hand, *Helicobacter pylori*, which is a bacteria present in the stomach, has been known to cause chronic gastritis, gastric ulcers, duodenal ulcers and the like, and a number of patients with gastrointestinal damages are infected with *H. pylori*. Therefore, these patients should take antibiotics such as clarithromycin, amoxicillin, metronidazole and tetracycline, together with anti-ulcer agents such as a proton pump inhibitor, or a gastric pump antagonist. Consequently, various side effects have been reported.

Therefore, there is a need to develop anti-ulcer drugs which inhibit the secretion of gastric acid (e.g., proton pump inhibitory activity) and enhance the protective factors (e.g., an increase in mucus secretion) while having eradication activity against *Helicobacter pylori* (*H. pylori*) at the same time.

Related Korean Patent No. 10-1613245 discloses that a 4-methoxypyrrole derivative or a pharmaceutically acceptable salt thereof has excellent anti-ulcer activity (i.e., proton pump inhibitory activity, etc.) and eradication activity against *Helicobacter pylori* (*H. pylori*), and thus can be effectively used for the prevention and treatment of gastrointestinal damage due to gastrointestinal track ulcers, gastritis, reflux esophagitis or *Helicobacter pylori*.

Specifically, in the above patent, the following compound is described as one of the 4-methoxypyrrole derivatives.

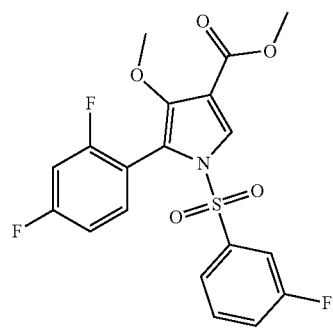 [SMILES: COC(=O)c1cn(S(=O)(=O)c2cccc(F)c2)c(-c2ccc(F)cc2F)c1OC]

According to the description of the above patent, the manufacturing process of the compound consists of four steps in total (For reference, in Example 8 of Korean Patent No. 10-1613245, the manufacturing process of the compound substantially consists of four steps of (step 8-4) to (step 8-7), except for the raw material preparation process of (step 8-1) to (step 8-3)).

However, the manufacturing process of the patent has a low yield of 51.4% when manufacturing in four steps in total, and uses hazardous reagents (e.g., sodium hydride, diisobutylaluminum hydride, etc.) and environmental polluting reagents (e.g., pyridinium chlorochromate), so it is not suitable for industrial mass production.

The present inventors constitute the manufacturing process in four steps in total, and they have confirmed that even when the use of hazardous reagents and environmental polluting reagents is excluded during the manufacturing process, the compound is obtained in a higher yield compared to the above patent, thereby completing the present invention.

DETAILED DESCRIPTION OF THE INVENTION

Technical Problem

In the present disclosure, there is provided a manufacturing method for 4-methoxypyrrole derivatives.

Technical Solution

In the present disclosure, there is provided a manufacturing method such as the following Reaction Scheme 1.

[Reaction Scheme 1]

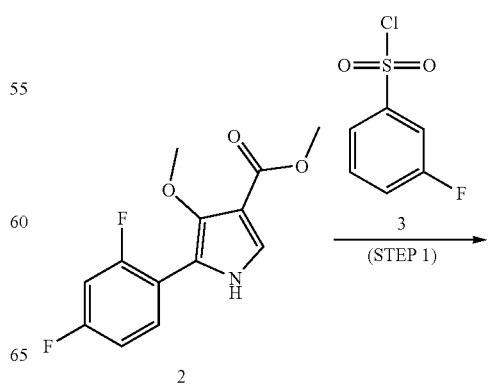

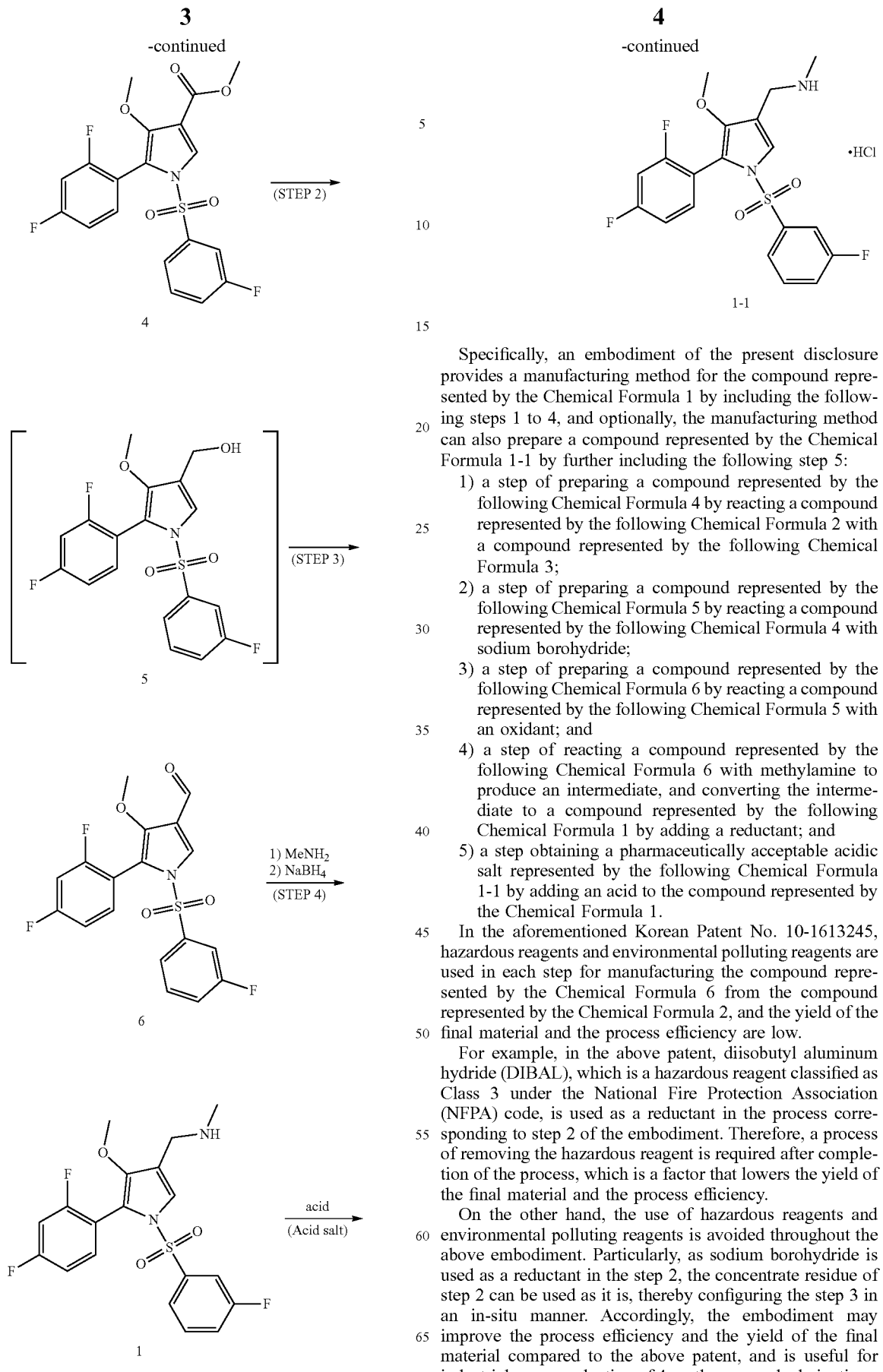

Specifically, an embodiment of the present disclosure provides a manufacturing method for the compound represented by the Chemical Formula 1 by including the following steps 1 to 4, and optionally, the manufacturing method can also prepare a compound represented by the Chemical Formula 1-1 by further including the following step 5:

1) a step of preparing a compound represented by the following Chemical Formula 4 by reacting a compound represented by the following Chemical Formula 2 with a compound represented by the following Chemical Formula 3;
2) a step of preparing a compound represented by the following Chemical Formula 5 by reacting a compound represented by the following Chemical Formula 4 with sodium borohydride;
3) a step of preparing a compound represented by the following Chemical Formula 6 by reacting a compound represented by the following Chemical Formula 5 with an oxidant; and
4) a step of reacting a compound represented by the following Chemical Formula 6 with methylamine to produce an intermediate, and converting the intermediate to a compound represented by the following Chemical Formula 1 by adding a reductant; and
5) a step obtaining a pharmaceutically acceptable acidic salt represented by the following Chemical Formula 1-1 by adding an acid to the compound represented by the Chemical Formula 1.

In the aforementioned Korean Patent No. 10-1613245, hazardous reagents and environmental polluting reagents are used in each step for manufacturing the compound represented by the Chemical Formula 6 from the compound represented by the Chemical Formula 2, and the yield of the final material and the process efficiency are low.

For example, in the above patent, diisobutyl aluminum hydride (DIBAL), which is a hazardous reagent classified as Class 3 under the National Fire Protection Association (NFPA) code, is used as a reductant in the process corresponding to step 2 of the embodiment. Therefore, a process of removing the hazardous reagent is required after completion of the process, which is a factor that lowers the yield of the final material and the process efficiency.

On the other hand, the use of hazardous reagents and environmental polluting reagents is avoided throughout the above embodiment. Particularly, as sodium borohydride is used as a reductant in the step 2, the concentrate residue of step 2 can be used as it is, thereby configuring the step 3 in an in-situ manner. Accordingly, the embodiment may improve the process efficiency and the yield of the final material compared to the above patent, and is useful for industrial mass production of 4-methoxypyrrole derivatives.

Hereinafter, an embodiment of the present invention will be described in detail for each step. Referring to the description below, it is also possible to control the quality of the final material by adjusting the process temperature and time of each step.

(Step 1)

The step 1 is to prepare a compound represented by the Chemical Formula 4 by reacting a compound represented by the Chemical Formula 2 with a compound represented by the Chemical Formula 3, and introduce a substituted phenylsulfonyl group to a pyrrole group of the compound represented by the Chemical Formula 2.

The reaction of step 1 may be performed in the presence of a base and 4-(dimethylamino)-pyridine. Herein, N,N-diisopropylethylamine, triethylamine, diisopropylamine, diisopropylethylamine, potassium carbonate, potassium hydrogen carbonate, sodium carbonate, sodium hydrogen carbonate, sodium hydroxide, potassium hydroxide, lithium hydroxide, sodium methylate, potassium butyrate, cesium carbonate, or a mixture of two or more thereof may be used as the base, and specifically, N,N-diisopropylethylamine may be used.

This is distinguished from Korean Patent No. 10-1613245 in which the process corresponding to step 1 is performed in the presence of sodium hydride. Specifically, the sodium hydride is a hazardous reagent corresponding to Class 3 under the National Fire Protection Association (NFPA) code, which classifies the risk in five levels from 0 (not dangerous) to 4 (very dangerous). Accordingly, the patent is not suitable for industrial mass production.

On the other hand, reagents used in step 1 including the base such as N,N-diisopropylethylamine, and 4-(dimethylamino)-pyridine are not designated as hazardous substances by the National Fire Protection Association (NFPA), and correspond to conventional reaction reagents. Accordingly, the embodiment of the present disclosure is suitable for industrial mass production by performing the reaction of step 1 in the presence of a base such as N,N-diisopropylethylamine and 4-(dimethylamino)-pyridine.

In the step 1, a solvent advantageous for dispersion of a base such as N,N-diisopropylethylamine, and 4-(dimethylamino)-pyridine may be used, and acetonitrile, tetrahydrofuran, methylene chloride, methanol, ethanol, propanol, iso-propanol, butanol, tert-butanol, or a mixture of two or more thereof may be used as the reaction solvent. Specifically, acetonitrile may be used as the reaction solvent of step 1.

In the step 1, a molar ratio of the compound represented by the Chemical Formula 2 and the compound represented by the Chemical Formula 3 may be 10:1 to 1:10, specifically 5:1 to 1:5, more specifically 3:1 to 1:3.

The reaction of step 1 may be performed at 10 to 35° C. Specifically, heat may be generated during the reaction of step 1, and cooling by an external device may be required to lower the reaction temperature to less than 10° C. If the reaction temperature is lower than 10° C., 80% or more of the starting material may remain, resulting in a lower yield of the final material.

However, when the reaction of step 1 is continued without cooling by an external device, the reaction may be possible in a temperature range of 10 to 35° C., for example, 20 to 35° C. This range increases a conversion rate of step 1 and may contribute to reducing the content of related substances in the final material.

The reaction of step 1 may be performed for 30 minutes to 5 hours. If the reaction time is less than 30 minutes, there is a problem that the reaction does not proceed sufficiently, thereby lowering the production yield. If the reaction time exceeds 5 hours, the production yield does not substantially increase. More specifically, the reaction may be performed for 1 hour to 3 hours.

After the reaction of step 1 is terminated, a step of purifying the compound represented by the Chemical Formula 4 may be included, if necessary. More specifically, the purification may be performed by crystallizing the compound represented by the Chemical Formula 4 from the reaction product of step 1.

As a solvent for crystallizing the compound represented by the Chemical Formula 4 from the reaction product of step 1, ethyl acetate may be used. For example, the crystallization may be performed by adding ethyl acetate to the reaction product of step 1 at a temperature of 5 to 30° C., followed by stirring for 10 minutes to 2 hours.

Thereafter, optionally, additional purification may be performed using an alcohol having 1 to 4 carbon atoms alone. Herein, the alcohol having 1 to 4 carbon atoms may be methanol, ethanol, propanol, iso-propanol, butanol, tert-butanol, or a mixture of two or more thereof, and more specifically, methanol may be used alone. For example, after firstly purifying the reaction product of step 1 using ethyl acetate under the above-described conditions, methanol may be additionally added. Subsequently, the temperature is raised to 40 to 70° C., cooled down to 20 to 30° C., and then stirred for 10 minutes to 2 hours.

After the compound represented by the Chemical Formula 4 is purified, it may be dried at 40 to 60 °C for 10 to 14 hours to lower the moisture content contained therein.

More specifically, when the moisture content of the compound represented by the Chemical Formula 4 is significantly lowered by drying at 50 to 60° C., a conversion rate of the subsequent step (i.e., step 2 below) may be increased.

(Steps 2 and 3)

The step 2 is to prepare a compound represented by the Chemical Formula 5 by reducing the compound represented by the following Chemical Formula 4. In addition, the step 3 is to prepare a compound represented by the Chemical Formula 6 by oxidizing the compound represented by the Chemical Formula 5.

As mentioned above, the use of sodium borohydride as a reductant in the step 2 excludes the use of hazardous reagents and environmental polluting reagents, the concentrate residue of step 2 can be used as it is, thereby configuring the step 3 in an in-situ manner.

The reaction of step 2 may be performed in an organic solvent such as dimethylacetamide, tetrahydrofuran, dimethyl sulfoxide, toluene, methanol, ethanol, dichloromethane, or a mixture of two or more thereof. Specifically, it may be performed using tetrahydrofuran as a solvent.

The reaction of step 2 may be performed in the presence of zinc chloride and dimethylaniline. Each of the zinc chloride and the dimethylaniline controls reactivity of the reduction reaction in step 2 to reduce side reactions and assists in the formation of the compound represented by the Chemical Formula 5. When they are present, the reaction efficiency of step 2 may be improved.

Herein, a molar ratio of the compound represented by the Chemical Formula 4 with the zinc chloride and the dimethylaniline may be 10:1 to 1:10, respectively. In other words, the zinc chloride and the dimethylaniline may be mixed to satisfy a molar ratio of the compound represented by the Chemical Formula 4 and the zinc chloride of 10:1 to 1:10, and a molar ratio of the compound represented by the Chemical Formula 4 and the dimethylaniline of 10:1 to 1:10 at the same time, and then used in step 2. Specifically, each molar ratio may be 5:1 to 1:5, more specifically 3:1 to 1:3.

Independently, a molar ratio of the compound represented by the Chemical Formula 4 and sodium borohydride may be 10:1 to 1:10, specifically 5:1 to 1:5, more specifically 3:1 to 1:3.

Specifically, after stirring the compound represented by the Chemical Formula 4 and the solvent in a reactor at room temperature, the temperature inside the reactor was lowered to −10 to 0° C., and the zinc chloride and the dimethylaniline are sequentially added and stirred. Subsequently, sodium borohydride may be added as a reductant while maintaining the temperature inside the reactor.

After the addition of the sodium borohydride, the temperature inside the reactor is increased to 55 to 80° C. and stirred, so that the reaction between the compound represented by the Chemical Formula 4 and the sodium borohydride may proceed. If the reaction temperature is less than −15° C., there is a problem that the production yield is lowered, and if the reaction temperature is more than 80° C., there is a problem that the reaction is not completed due to reduction of zinc.

For example, the reaction temperature may be 55 to 65° C. Within the above temperature range, the reduction of zinc is suppressed, and the conversion to the compound represented by the Chemical Formula 5 may be completed through the reaction.

The reaction of the compound represented by the Chemical Formula 4 and the sodium borohydride may be performed for 30 minutes to 48 hours. If the reaction time is less than 30 minutes, there is a problem that the reaction does not proceed sufficiently, thereby lowering the production yield. If the reaction time exceeds 48 hours, the production yield does not substantially increase. More specifically, the reaction may be performed for 1 hour to 24 hours.

Since hydrogen and heat may be generated by the reaction of the compound represented by the Chemical Formula 4 and the sodium borohydride, the reactor may be cooled until the temperature inside the reactor reaches −5 to 5° C. after completion of the reaction in step 2.

For example, when cooling the reactor until the temperature inside the reactor reaches −5 to 0° C., the safety in the production scale may be improved.

After cooling the temperature inside the reactor, a step of purifying the compound represented by the Chemical Formula 5 may be included, if necessary. More specifically, the purification may be performed by crystallizing the compound represented by the Chemical Formula 5 from the reaction product of step 2.

As a solvent for crystallizing the compound represented by the Chemical Formula 5 from the reaction product of step 2, methanol and water may be used. For example, the crystallization may be performed by adding methanol to the reaction product of step 2 at a temperature of 0 to 25° C., followed by water at a temperature of 20 to 25° C., and then stirring for 10 minutes to 2 hours.

Thereafter, optionally, additional purification may be performed using water and an aqueous hydrochloric acid solution. For example, after firstly purifying the reaction product of step 2 using water and ethyl acetate under the above-described conditions, water and an aqueous hydrochloric acid solution may be additionally added, followed by stirring at 20 to 30° C. for 10 minutes to 2 hours.

Meanwhile, the step 3 is to prepare a compound represented by the Chemical Formula 6 by oxidizing the compound represented by the Chemical Formula 5. Herein, an oxidant catalyst and a solvent may be added to the concentrated residue according to step 2 such that the steps 2 and 3 are performed in an in-situ manner.

Specifically, oxidation of an alcohol group of the compound represented by the Chemical Formula 5 may be performed in the presence of
1) an oxidant selected from (diacetoxyiodo)benzene, iodine, iodobenzene dichloride, iodosylbenzene, and trichloroisocyanuric acid;
2) a catalyst selected from (2,2,6,6-tetramethylpiperidin-1-yl)oxyl, 4-acetamido-2,2,6,6-tetramethylpiperidine 1-oxyl, 4-hydroxy-2,2,6,6-tetramethylpiperidine 1-oxyl, 4-methacryloyloxy-2,2,6,6-tetramethylpiperidine-1-oxyl, 4-oxo-2,2,6,6-tetramethyl-1-piperidinyloxy, 4-amino-2,2,6,6-tetramethylpiperidin-1-oxyl, 4-carboxy-2,2,6,6-tetramethylpiperidine 1-oxyl, 4-hydroxy-2,2,6,6-tetramethylpiperidine 1-oxyl benzoate, 4-(2-iodoacetamido)-2,2,6,6-tetramethyl-1-piperidinyloxy, 4-maleimido-2,2,6,6-tetramethyl-1-piperidinyloxy, 4-isothiocyanato-2,2,6,6-tetramethylpiperidine 1-oxyl, 4-methoxy-2,2,6,6-tetramethyl-1-piperidinyloxy, and 4-phosphonooxy-2,2,6,6-tetramethyl-1-piperidinyloxy; or a mixture of one oxidant selected from 1) and one catalyst selected from 2).

More specifically, (diacetoxyiodine)benzene and (2,2,6,6-tetramethylpiperidin-1-yl)oxyl may be added to the concentrated residue according to step 2. In this case, a molar ratio of the compound represented by the Chemical Formula 5 with the (diacetoxyiodo)benzene and (2,2,6,6-tetramethylpiperidin-1-yl)oxyl may be 10:1 to 1:10, respectively.

In other words, the (diacetoxyiodo)benzene and the (2,2,6,6-tetramethylpiperidin-1-yl)oxyl may be mixed to satisfy a molar ratio of the compound represented by the Chemical Formula 5 and the (diacetoxyiodo)benzene of 10:1 to 1:10, and a molar ratio of the compound represented by the Chemical Formula 5 and the (2,2,6,6-tetramethylpiperidin-1-yl)oxyl of 10:1 to 1:10 at the same time, and then used for the oxidation of step 3.

The reaction of step 3 may use an organic solvent such as dichloromethane, dichloroethane, acetonitrile, ethyl acetate, methanol, toluene, dimethylformamide, dimethyl sulfoxide, tetrahydrofuran, or a mixture of two or more thereof. Specifically, it may use dichloromethane as a solvent.

The reaction temperature in step 3 may be 10 to 40° C. If the reaction temperature is less than 10° C., there is a problem that the production yield is lowered. If the reaction temperature exceeds 40° C., the production yield does not substantially increase. More specifically, the reaction may be performed at a temperature of 20 to 30° C.

The reaction of step 3 may be performed for 5 minutes to 5 hours. If the reaction time is less than 5 minutes, there is a problem that the reaction does not proceed sufficiently, thereby lowering the production yield. If the reaction time exceeds 5 hours, the production yield does not substantially increase. More specifically, the reaction may be performed for 5 minutes to 3 hours.

After the reaction of step 3 is terminated, a step of purifying the compound represented by the Chemical Formula 6 may be included, if necessary. More specifically, the purification may be performed by crystallizing the compound represented by the Chemical Formula 6 from the reaction product of step 3. As the crystallization solvent, an alcohol having 1 to 4 carbon atoms and water may be mixed and used. Herein, the alcohol having 1 to 4 carbon atoms may be methanol, ethanol, propanol, iso-propanol, butanol, tert-butanol, or a mixture of two or more thereof. More specifically, as a solvent for crystallizing the compound represented by the Chemical Formula 6 from the reaction product of step 3, a mixture of ethanol and water may be used. For example, the crystallization may be performed by adding an aqueous ethanol solution to the reaction product of step 3 at a temperature of 20 to 30° C., followed by stirring for 10 minutes to 2 hours.

After the compound represented by the Chemical Formula 6 is purified, it may be dried to lower the moisture content contained therein.

For example, when drying at a temperature of 40 to 50° C. for 12 hours to 18 hours, the moisture content of the compound represented by the Chemical Formula 6 is significantly lowered, thereby increasing reactivity of the subsequent reductive amination reaction (i.e., step 4 below).

(Step 4)

The step 4 is to convert the compound represented by the Chemical Formula 6 to the compound represented by the Chemical Formula 1 by using a reductive amination reaction.

Specifically, in the step 4, the compound represented by the Chemical Formula 6 produces an imine compound by an imine reaction with methylamine. Since the imine compound corresponds to an intermediate having an unstable structure, it can be easily converted into a compound represented by the Chemical Formula 1 by a reduction reaction.

The reductive amination reaction of step 4 may be performed in a reaction solvent of methanol, ethanol, isopropanol, dichloromethane, dichloroethane, tetrahydrofuran, ethyl acetate, dimethyl ether, acetonitrile, or a mixture of two or more thereof.

More specifically, as the compound represented by the Chemical Formula 6 and the methylamine are added together with the reaction solvent in a separate reactor different from step 3 and stirred at 10 to 30° C. for 20 minutes to 2 hours, the compound represented by the Chemical Formula 6 and the methylamine may be reacted in a state sufficiently dissolved in the solvent, thereby producing an imine compound.

Herein, the stirring time and temperature may be adjusted in consideration that the content of related substances in the final material may increase as solubility of the compound represented by the Chemical Formula 6 decreases. For example, when stirring at 10 to 15° C. for 30 minutes to 1 hour, the compound represented by the Chemical Formula 6 may be sufficiently dissolved, and the content of related substances in the final material may decrease when the reaction proceeds in this state.

Meanwhile, the reduction reaction of the intermediate (i.e., imine compound) produced by the reaction of the compound represented by the Chemical Formula 6 and methylamine may proceed more stably at a low temperature.

In consideration of this, after the reaction of the compound represented by the Chemical Formula 6 with methylamine is terminated, the reactor is cooled until it reaches a temperature in the range of −10 to 0° C., for example −10° C. to −5° C. Thereafter, the reductant is added in the above-described temperature range, and stirred while maintaining the reactor temperature at −5 to 10° C., for example −5 to 0° C. In such a low temperature range, the intermediate (i.e., imine compound) may stably react with the reductant to be converted to the compound represented by the Chemical Formula 1.

Herein, sodium borohydride may be used as the reductant. A molar ratio of the compound represented by the Chemical Formula 6 and the methylamine may be 10:1 to 1:10, and a molar ratio of the compound represented by the Chemical Formula 6 and the sodium borohydride may be 10:1 to 1:10. Specifically, each molar ratio may be 5:1 to 1:5, more specifically 3:1 to 1:3.

After sufficiently reacting the intermediate (i.e., imine compound) with the reductant, an acid aqueous solution containing hydrochloric acid, glutamic acid, malonic acid, succinic acid, tartaric acid, oxalic acid, fumaric acid, phosphoric acid, methanesulfonic acid, or a mixture of two or more thereof may be supplied to adjust the pH in order to terminate the reaction (work-up). For example, the pH may be adjusted to 6.7 to 7.3 by supplying an aqueous hydrochloric acid solution of 5 to 7 N.

Thereafter, extraction may be performed 1 to 3 times using an organic solvent to obtain an organic layer, and a drying agent may be added to the organic layer, stirred, and then filtered under reduced pressure. Then, the filtrate may be washed, and concentrated under reduced pressure.

In the extraction, an organic solvent such as ethyl acetate, diethyl ether, dimethyl ether, diisopropyl ether, methyl tertiary butyl ether, acetone, methyl ethyl ketone, methyl isobutyl ketone, or a mixture of two or more thereof may be used.

Further, examples of the drying agent used after the extraction may include magnesium sulfate, sodium sulfate, and the like.

(Step 5)

The compound represented by the Chemical Formula 1 may be in the form of a pharmaceutically acceptable salt. The salt includes conventional acid addition salts, for example, salts derived from inorganic acids such as hydrochloric acid, hydrobromic acid, sulfuric acid, sulfamic acid, phosphoric acid, or nitric acid, and salts derived from organic acids such as acetic acid, propionic acid, succinic acid, glycolic acid, stearic acid, maleic acid, hydroxy maleic acid, phenylacetic acid, glutamic acid, benzoic acid, salicylic acid, sulfanylic acid, 2-acetoxy-benzoic acid, fumaric acid, toluenesulfonic acid, methanedisulfonic acid, ethandisulfonic acid, oxalic acid, or trifluoroacetic acid. Preferably, the salt may be hydrochloride or fumarate.

In order to supply the compound represented by the Chemical Formula 1 in the form of a pharmaceutically acceptable salt, step 5 of obtaining a pharmaceutically acceptable acidic salt represented by the Chemical Formula 1-1 by adding an acid to the compound represented by the Chemical Formula 1 may be further included after the step 4:

[Chemical Formula 1-1]

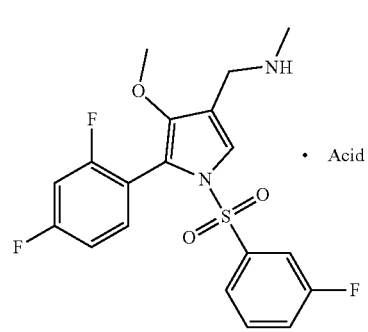 [SMILES: CNCc1cn(S(=O)(=O)c2cccc(F)c2)c(-c2ccc(F)cc2F)c1OC ; Cl]

Specifically, the step 5 may include a step of crystallizing the acidic salt represented by the Chemical Formula 1-1 by supplying an organic solvent to the compound represented by the Chemical Formula 1, and then supplying an acid or a mixed solution thereof with an organic solvent.

More specifically, an organic solvent may be supplied to the concentrated residue of step 4 containing the compound represented by the Chemical Formula 1. The organic solvent supplied at this time may be ethyl acetate, diethyl ether, dimethyl ether, diisopropyl ether, methyl tertiary butyl ether, acetone, methyl ethyl ketone, methyl isobutyl ketone, methanol, ethanol, isopropyl alcohol, acetonitrile, dichloromethane, normal hexane, or a mixture of two or more of thereof. For example, it may be ethyl acetate.

After supplying the organic solvent to the concentrated residue of step 4 containing the compound represented by the Chemical Formula 1, followed by stirring, the temperature inside the reactor is adjusted to −15° C. to 20° C., and the acid or the mixed solution thereof with an organic solvent is supplied. Thereafter, the acidic salt represented by the Chemical Formula 1-1 may be crystallized by stirring in the adjusted temperature range.

The acid or the mixed solution thereof with an organic solvent used to crystallize the acidic salt represented by the Chemical Formula 1-1 may be hydrochloric acid, glutamic acid, malonic acid, succinic acid, tartaric acid, oxalic acid, fumaric acid, phosphoric acid, methanesulfonic acid, or a mixture of two or more thereof; or a mixed solution thereof with an organic solvent. The organic solvent in the mixed solution may be selected from the organic solvents presented above. For example, a mixed solution in which ethyl acetate, diethyl ether, or a mixture thereof is used as the organic solvent, and hydrochloric acid is dissolved therein at a concentration of 0.5 to 2.0 M may be used to crystallize the acidic salt represented by the Chemical Formula 1-1.

The temperature range of −15° C. to 20° C. for crystallization of the acidic salt represented by the Chemical Formula 1-1 is determined in consideration of the fact that the production yield does not substantially increase when the reaction temperature is less than −15° C., and the production yield may be lowered when the reaction temperature exceeds 20° C.

In addition, in order to crystallize the acidic salt represented by the Chemical Formula 1-1, the acid or the mixed solution thereof with an organic solvent is supplied and then stirred for at least 1 hour. And, the stirring time may be controlled to 12 hours or less in order to prevent precipitation of related substances during stirring.

In the step 5, the crystallization of the acidic salt represented by the Chemical Formula 1-1 may be performed twice or more.

For example, after crystallizing the acidic salt represented by the Chemical Formula 1-1, the acidic salt represented by the Chemical Formula 1-1 is extracted using the organic solvent. Thereafter, the acid or the mixed solution thereof with an organic solvent is supplied and stirred for at least 4 hours for recrystallization of the acidic salt represented by the Chemical Formula 1-1. Herein, the stirring may be performed for 12 hours or less in order to prevent precipitation of related substances during stirring.

The recrystallization is for purification, and the same organic solvent; and the same acid or a mixed solution thereof with an organic solvent as used for the crystallization may be used.

In addition, during the recrystallization process, a base may be additionally used for dissociation of the acid salt. Herein, potassium carbonate, potassium hydrogen carbonate, sodium carbonate, sodium hydrogen carbonate, sodium hydroxide, potassium hydroxide, lithium hydroxide, sodium methylate, potassium butyrate, cesium carbonate, or a mixture of two or more thereof may be used as the base for dissociation of the acid salt. Specifically, sodium hydrogen carbonate may be used, and a method of using the same may follow what is known in the art.

Meanwhile, there is provided a pharmaceutical composition for the prevention or treatment of gastrointestinal damage due to gastrointestinal tract ulcers, gastritis, reflux esophagitis or *Helicobacter pylori* (*H. pylori*), containing the compound represented by Chemical Formula 1 or a pharmaceutically acceptable salt thereof.

Also, there is provided a pharmaceutical composition for the prevention or treatment of 5-HT receptor-mediated or muscarinic acetylcholine receptor-mediated diseases containing the compound represented by Chemical Formula 1 or a pharmaceutically acceptable salt thereof. In this case, the 5-HT receptor-mediated or muscarinic acetylcholine receptor-mediated diseases may be depression, manic depression, schizophrenia, autism, obsessive-compulsive neurosis, anxiety disorder, migraine, hypertension, eating disorder, irritable bowel syndrome (IBS), peptic ulcer, diabetic neuropathy, asthma, or overactive bladder.

The pharmaceutical composition may include a commonly used pharmaceutically acceptable carrier such as excipients, disintegrants, sweetening agents, lubricants or flavoring agents. The pharmaceutical composition may be formulated into preparations for oral administration such as tablets, capsules, powders, granules, suspensions, emulsions or syrups; or preparations for parenteral administration such as injections in accordance with conventional methods. The preparations can be formulated into various forms, for example, in a single dosage form or multiple dosage forms.

The pharmaceutical composition may be orally or non-orally administered. The non-oral administration may include, for example, intravenous, intraperitoneal, subcutaneous, rectal, and local administration. The composition may preferably be administered orally. Therefore, the composition may be formulated into various forms such as tablets, capsules, aqueous solutions or suspensions. In the case of tablets for oral administration, a carrier such as lactose or corn starch and a lubricant such as magnesium stearate may be commonly added. In the case of capsules for oral administration, lactose and/or dried corn starch may be used as a diluent. When an aqueous suspension is required for oral use, active ingredients may be combined with emulsions and/or suspensions. If necessary, certain sweetening and/or flavoring agents may be added. For intramuscular, intraperitoneal, subcutaneous and intravenous administration, sterile solutions of active ingredients are usually prepared, and the pH of the solutions should be suitably adjusted and buffered. For intravenous administration, the total concentration of solutes should be controlled in order to render the preparation isotonic. The composition according to the present disclosure may be in the form of an aqueous solution containing a pharmaceutically acceptable carrier such as saline with a pH of 7.4. The solution may be introduced into a patient's intramuscular blood-stream by local bolus injection.

In this case, the pharmaceutical composition may be administered in a therapeutically effective amount. Therefore, the compound represented by Chemical Formula 1 or a pharmaceutically acceptable salt thereof contained in the pharmaceutical composition may be administered in an effective amount ranging from about 0.01 mg/kg to about 100 mg/kg per day to a subject patient. Of course, the dosage may be changed according to the patient's age, weight, susceptibility, symptom or the efficacy of the compound.

Advantageous Effects

As described above, the embodiment of the present disclosure is useful for industrial mass production of 4-methoxypyrrole derivatives, because the process efficiency and yield are improved, and the use of hazardous reagents and environmental polluting reagents is avoided.

Detailed Description of the Embodiments

Hereinafter, the present invention will be described in more detail by the following examples. However, the following examples are for illustrative purposes only, and the scope of the present invention is not limited thereto.

Analysis of the compounds prepared in the following Examples was performed as follows: Nuclear magnetic resonance (NMR) spectrum analysis was performed on a Bruker 400 MHz spectrometer, chemical shift was analyzed in ppm, and column chromatography was performed on silica gel (Merck, 70-230 mesh) (W. C. Still, *J. Org. Chem.*, 1978 (43), 2923-2925).

Example1

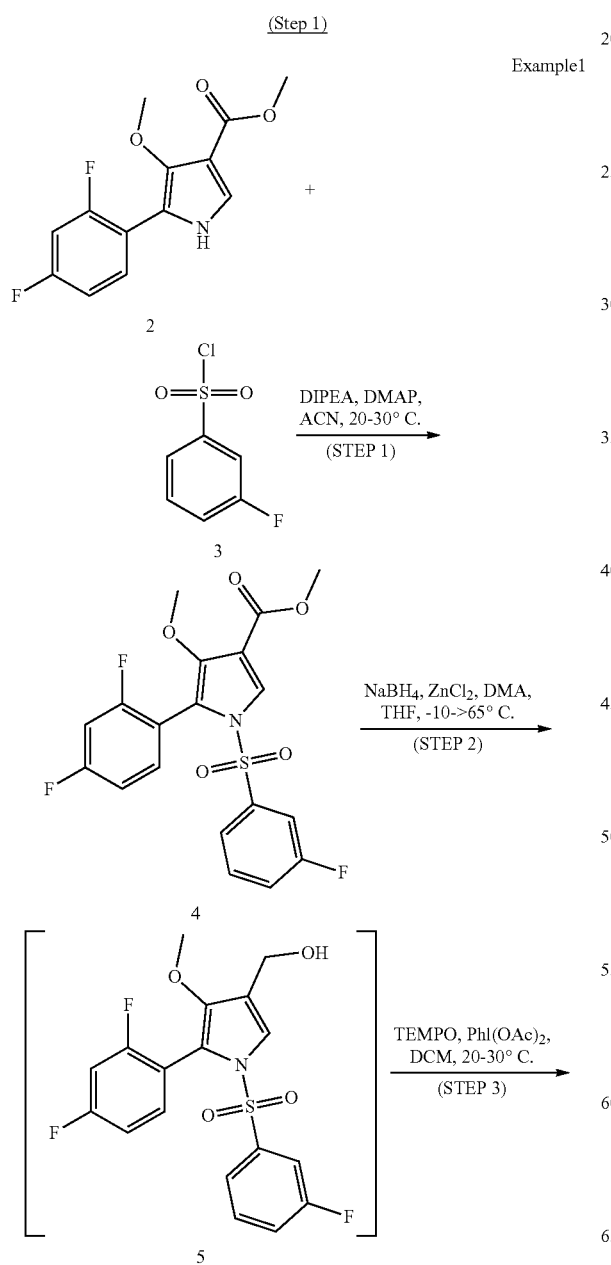

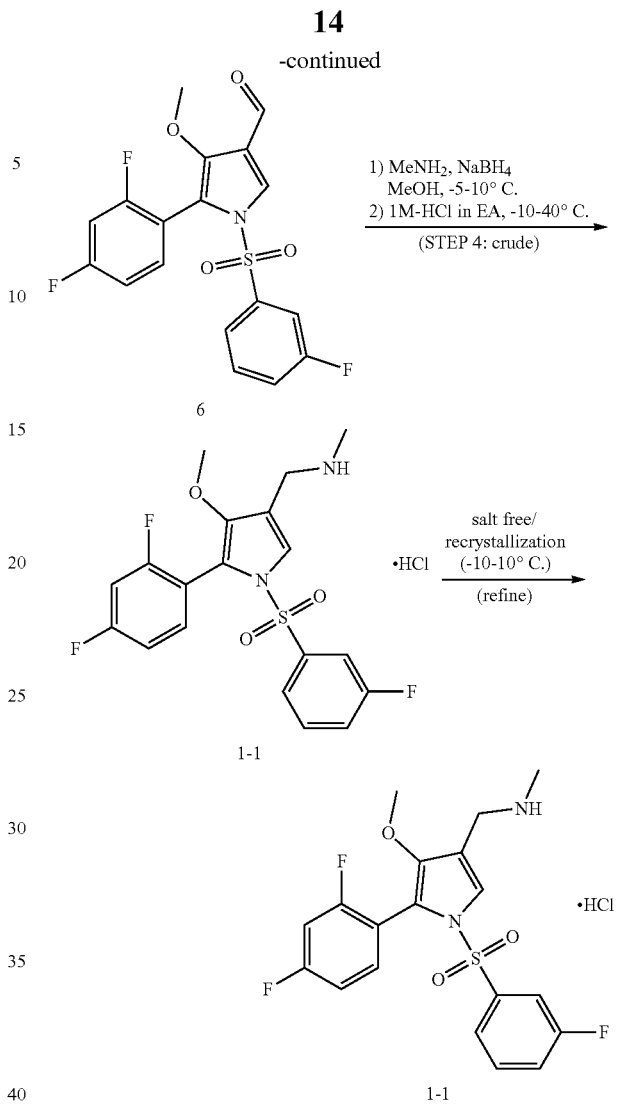

100.0 g of methyl 5-(2,4-difluorophenyl)-4-methoxy-1H-pyrrole-3-carboxylate (Chemical Formula 2), 9.2 g of 4-(dimethylamino)-pyridine, 393.0 g of acetonitrile were added to a flask, and stirred at room temperature for 10 minutes. After cooling the temperature inside the flask to 5 to 10° C., 80.1 g of 3-fluorobenzenesulfonyl chloride (Chemical Formula 3) and 53.2 g of N,N-diisopropylethylamine were added, and stirred at a temperature of 20 to 30° C. for 2 hours to complete the reaction.

Then, 500.0 g of purified water and 451.0 g of ethyl acetic acid were added, stirred for 10 minutes, and allowed to stand for 10 minutes. Thereafter, the aqueous layer was discarded.

Thereafter, 500.0 g of purified water was added to the organic layer, and a 1N-aqueous hydrochloric acid solution was gradually added within the temperature range of 20 to 30° C. to adjust the pH to 3.5 to 5.0, followed by stirring for 10 minutes and allowed to stand for 10 minutes. Then, the resulting aqueous layer was discarded.

Then, the organic layer was concentrated under reduced pressure at 50 to 55° C., and 158.4 g of methanol was added at an internal temperature of 20 to 30° C., followed by stirring for 10 minutes. Subsequently, the organic layer was concentrated under reduced pressure at 50 to 55° C., and 396.0 g of methanol was added at an internal temperature of 20 to 30° C., followed by stirring for 1 hour. While maintaining the internal temperature of 20 to 30° C., 300.0 g of purified water was added over 20 minutes and stirred for 1 hour. The crystals thus produced were filtered under reduced pressure, and the filtrate was washed with 200.0 g of purified water.

The filtrate thus washed was put in a dryer, and then vacuum-dried at a temperature of 40 to 45° C. for 12 hours or more to obtain 154.4 g of a compound represented by Chemical Formula 4 (yield: 97.0%).

$^1$H-NMR (500 MHZ, MeOD): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)
(Step 2)

100.0 g of the compound represented by Chemical Formula 4 obtained in the step 1 and 444.5 g of tetrahydrofuran were added to a new flask, stirred at 20 to 30° C. for 10 minutes, and then cooled down to an internal temperature of −10 to −5° C. After 32.1 g of zinc chloride was added to the resulting solution over 5 minutes and stirred for 10 minutes, 28.5 g of N,N-dimethylaniline was added, followed by stirring.

Thereafter, 8.9 g of sodium borohydride was divided into three and added over 5 minutes at an internal temperature of −10 to 0° C., followed by stirring for 10 minutes three times.

Then, the reaction was completed by stirring for 20 hours at an internal temperature of 60 to 65° C., and the internal temperature was cooled down to 0 to 5° C. In this reaction, the compound represented by the Chemical Formula 5 was produced.

Thereafter, 200.0 g of purified water was gradually added at an internal temperature of 0 to 15° C., and 451.0 g of ethyl acetate was added at an internal temperature of 20 to 30° C. Thereafter, 87.2 g of a 6N-aqueous hydrochloric acid solution was gradually added, stirred for 30 minutes, and allowed to stand for 10 minutes (the internal temperature was maintained at 20 to 30° C.), followed by discarding the aqueous layer by layer separation. Then, the organic layer was washed with 300.0 g of purified water and 10.9 g of a 6N-aqueous hydrochloric acid solution (the internal temperature was maintained at 20 to 30° C., and repeated twice), followed by discarding the aqueous layer by layer separation. Thereafter, 50.0 g of magnesium sulfate was added to the organic layer, stirred for 10 minutes, filtered under reduced pressure, and the filtrate was concentrated under reduced pressure at 50 to 55° C. Then, 265.3 g of methylene chloride was added, stirred for 10 minutes, and then concentrated under reduced pressure at 50 to 55° C.
(Step 3)

6.9 g of (2,2,6,6-tetramethylpiperidin-1-yl)oxyl, 86.1 g of (diacetoxyiodo)benzene, and 1,171.1 g of dichloromethane were added to the concentrated residue of step 2, and the reaction was completed by stirring for 2 hours at an internal temperature of 20 to 30° C., followed by adding 882.8 g of purified water. Thereafter, 679.7 g of a saturated aqueous sodium hydrogen carbonate solution (61.8 g of sodium hydrogen carbonate, 617.9 g of purified water) was gradually added, stirred for 10 minutes, and allowed to stand for 10 minutes, followed by discarding the aqueous layer after layer separation. 17.7 g of magnesium sulfate was added to the organic layer, stirred for 10 minutes, and then filtered under reduced pressure.

Then, after concentration under reduced pressure at 38 to 42° C., 513.6 g of an aqueous ethanol solution (390.0 g of ethanol, 123.6 g of purified water) was added thereto, followed by stirring at an internal temperature of 20 to 30° C. for 1 hour to crystallize.

The resulting crystals were filtered under reduced pressure, and the filtrate was washed with 174.3 g of an aqueous ethanol solution (132.3 g of ethanol, 41.9 g of purified water). The washed filtrate was put in a dryer and vacuum-dried at a temperature of 40 to 45° C. for 12 hours or more to obtain 83.9 g of a compound represented by Chemical Formula 6 (yield: 90.0%).

$^1$H-NMR (500 MHZ, MeOD): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)
(Step 4)

100.0 g of the compound represented by Chemical Formula 6 obtained in the step 3, 396.0 g of methanol, and 48.5 g of methylamine (9.8 M in methanol) were added to a new flask, and stirred for 30 minutes while adjusting the internal temperature to 20 to 30° C.

Thereafter, the internal temperature was cooled down to −5 to 0° C., and 4.8 g of sodium borohydride was dividedly added in a temperature range of −5 to 10° C., followed by stirring at −5 to 10° C. for 30 minutes to complete the reaction.

After completion of the reaction, 1,000 g of purified water was gradually added while maintaining an internal temperature of 10 to 15° C., and 902.0 g of ethyl acetate was added. Subsequently, the pH was adjusted to 6.7 to 7.3 using a 6N-aqueous hydrochloric acid solution while maintaining the internal temperature at 10 to 15° C.

Then, after stirring for 10 minutes, the mixture was allowed to stand for 30 minutes to separate the layers, and the organic layer was stored. 451.0 g of ethyl acetate was added to the resulting aqueous layer, stirred for 10 minutes, and then allowed to stand for 10 minutes. Thereafter, layer separation was performed, and the organic layer was combined with the organic layer obtained earlier, and the same re-extraction process was performed again.

Then, 600.0 g of aqueous sodium chloride solution (100.0 g of sodium chloride, 500.0 g of purified water) was added to the combined organic layer, stirred for 10 minutes, and allowed to stand for 10 minutes to separate the layers, followed by discarding the aqueous layer.

100.0 g of magnesium sulfate was added to the organic layer, stirred for 10 minutes while maintaining an internal temperature of 10 to 15° C., and then filtered under reduced pressure. The filtrate was washed with 270.6 g of ethyl acetate, and the filtrate was concentrated under reduced pressure at 38 to 42° C.
(Step 5)

90.2 g of ethyl acetate was added to the concentrated residue, stirred until a relatively uniform state, and 460.5 g of a 1.0M hydrochloric acid, ethyl acetate solution was gradually added at an internal temperature of −5 to 5° C. Then, the mixture was stirred at 0 to 5° C. for 12 hours to crystallize the compound represented by Chemical Formula 1-1.

The resulting crystals were filtered under reduced pressure, and the filtrate was washed with 90.2 g of ethyl acetate. 815.4 g of the filtrate and ethyl acetate were added to a new flask, cooled down to an internal temperature of 0 to 15° C., and stirred for 10 minutes. Thereafter, 976.3 g of aqueous sodium hydrogen carbonate solution (72.3 g of sodium hydrogen carbonate, 904.0 g of purified water) was added at an internal temperature of 10 to 15° C., stirred for 10 minutes, and allowed to stand for 30 minutes to separate the layers, followed by storing the organic layer.

407.7 g of ethyl acetate was added to the aqueous layer, stirred for 10 minutes, and allowed to stand for 10 minutes to separate the layers. The organic layer was combined with the organic layer obtained earlier, and the aqueous layer was re-extracted again in the same procedure and combined with the organic layer.

90.4 g of magnesium sulfate was added to the organic layer, stirred at an internal temperature of 10 to 15° C. for 10 minutes, and then filtered under reduced pressure. The filtrate was washed with 244.6 g of ethyl acetate, and the filtrate was concentrated under reduced pressure at 38 to 42° C.

After 81.5 g of ethyl acetate was added to the concentrated residue and stirred, 368.4 g of a 1.0M hydrochloric acid, ethyl acetate solution was gradually added at an internal temperature of −5 to 5° C., followed by stirring at 0 to 5° C. for 12 hours to recrystallize.

The resulting crystals were filtered under reduced pressure, and the filtrate was washed with 81.5 g of ethyl acetate. The resulting filtrate was put in a dryer, vacuum-dried at a temperature of 20 to 30° C. for 12 hours, and further dried for 6 hours by heating to 38 to 42° C. to obtain 90.7 g of a compound represented by Chemical Formula 1-1 (yield: 80.2%).

$^1$H-NMR (500 MHZ, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

Example 2

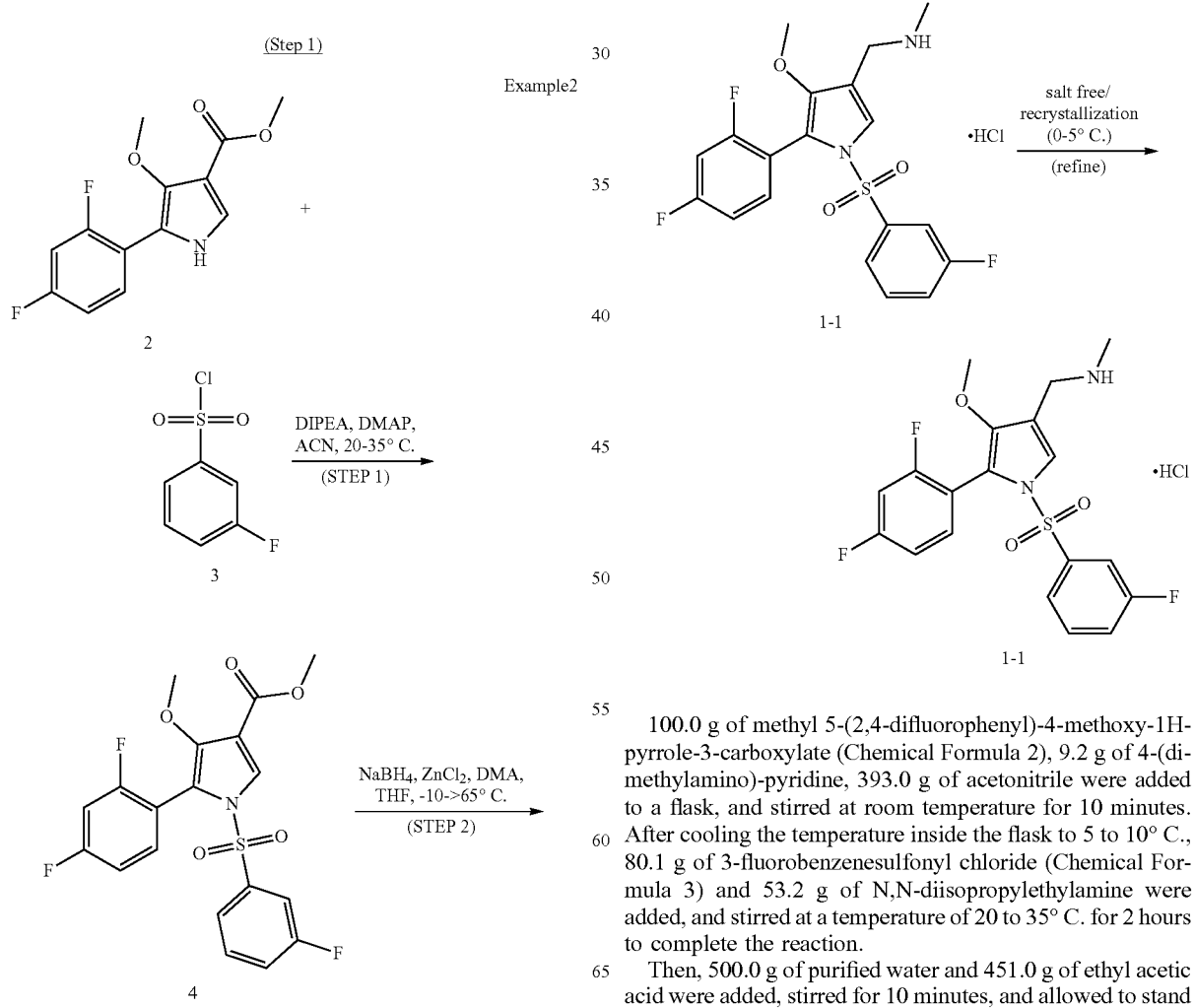

100.0 g of methyl 5-(2,4-difluorophenyl)-4-methoxy-1H-pyrrole-3-carboxylate (Chemical Formula 2), 9.2 g of 4-(dimethylamino)-pyridine, 393.0 g of acetonitrile were added to a flask, and stirred at room temperature for 10 minutes. After cooling the temperature inside the flask to 5 to 10° C., 80.1 g of 3-fluorobenzenesulfonyl chloride (Chemical Formula 3) and 53.2 g of N,N-diisopropylethylamine were added, and stirred at a temperature of 20 to 35° C. for 2 hours to complete the reaction.

Then, 500.0 g of purified water and 451.0 g of ethyl acetic acid were added, stirred for 10 minutes, and allowed to stand for 10 minutes. Thereafter, the aqueous layer was discarded.

Thereafter, 500.0 g of purified water was added to the organic layer, and a 1N-aqueous hydrochloric acid solution was gradually added within the temperature range of 20 to 30° ° C. to adjust the pH to 3.5 to 5.0, followed by stirring for 10 minutes and allowed to stand for 10 minutes. Then, the resulting aqueous layer was discarded.

Then, the organic layer was concentrated under reduced pressure at 50 to 55° C., and 158.4 g of methanol was added at an internal temperature of 20 to 30° C., followed by stirring for 10 minutes. Subsequently, the organic layer was concentrated under reduced pressure at 50 to 55° C., and 396.0 g of methanol was added at an internal temperature of 20 to 30° C., followed by stirring for 1 hour. While maintaining the internal temperature of 20 to 30° C., 300.0 g of purified water was added over 20 minutes and stirred for 1 hour. The crystals thus produced were filtered under reduced pressure, and the filtrate was washed with 200.0 g of purified water.

The filtrate thus washed was put in a dryer, and then vacuum-dried at a temperature of 50 to 60° C. for 12 hours or more to obtain 154.4 g of a compound represented by Chemical Formula 4 (yield: 97.0%).

$^1$H-NMR (500 MHZ, MeOD): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)

(Step 2)

100.0 g of the compound represented by Chemical Formula 4 obtained in the step 1 and 444.5 g of tetrahydrofuran were added to a new flask, stirred at 20 to 30° C. for 10 minutes, and then cooled down to an internal temperature of −10 to 0° C. After 32.1 g of zinc chloride was added to the resulting solution over 5 minutes and stirred for 10 minutes, 28.5 g of N,N-dimethylaniline was added, followed by stirring.

Thereafter, 8.9 g of sodium borohydride was divided into three and added over 5 minutes at an internal temperature of −10 to 0° C., followed by stirring for 10 minutes three times.

Then, the reaction was completed by stirring for 20 hours at an internal temperature of 55 to 65° C., and the internal temperature was cooled down to −5 to 0° C. In this reaction, the compound represented by the Chemical Formula 5 was produced.

Thereafter, 200.0 g of purified water was gradually added at an internal temperature of 0 to 25° C., and 451.0 g of ethyl acetate was added at an internal temperature of 20 to 25° C. Thereafter, 87.2 g of a 6N-aqueous hydrochloric acid solution was gradually added, stirred for 30 minutes, and allowed to stand for 10 minutes (the internal temperature was maintained at 20 to 30° C.), followed by discarding the aqueous layer by layer separation. Then, the organic layer was washed with 300.0 g of purified water and 10.9 g of a 6N-aqueous hydrochloric acid solution (the internal temperature was maintained at 20 to 30° C., and repeated twice), followed by discarding the aqueous layer by layer separation. Thereafter, 50.0 g of magnesium sulfate was added to the organic layer, stirred for 10 minutes, filtered under reduced pressure, and the filtrate was concentrated under reduced pressure at 50 to 55° C. Then, 265.3 g of methylene chloride was added, stirred for 10 minutes, and then concentrated under reduced pressure at 50 to 55° C.

(Step 3)

6.9 g of (2,2,6,6-tetramethylpiperidin-1-yl)oxyl, 86.1 g of (diacetoxyiodo)benzene, and 1,171.1 g of dichloromethane were added to the concentrated residue of step 2, and the reaction was completed by stirring for 2 hours at an internal temperature of 20 to 30° C., followed by adding 882.8 g of purified water. Thereafter, 679.7 g of a saturated aqueous sodium hydrogen carbonate solution (61.8 g of sodium hydrogen carbonate, 617.9 g of purified water) was gradually added, stirred for 10 minutes, and allowed to stand for 10 minutes, followed by discarding the aqueous layer after layer separation. 17.7 g of magnesium sulfate was added to the organic layer, stirred for 10 minutes, and then filtered under reduced pressure.

Then, after concentration under reduced pressure at 38 to 42° C., 513.6 g of an aqueous ethanol solution (390.0 g of ethanol, 123.6 g of purified water) was added thereto, followed by stirring at an internal temperature of 20 to 30° C. for 1 hour to crystallize.

The resulting crystals were filtered under reduced pressure, and the filtrate was washed with 174.3 g of an aqueous ethanol solution (132.3 g of ethanol, 41.9 g of purified water). The washed filtrate was put in a dryer and vacuum-dried at a temperature of 40 to 50° C. for 12 hours or more to obtain 83.9 g of a compound represented by Chemical Formula 6 (yield: 90.0%).

$^1$H-NMR (500 MHZ, MeOD): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)

(Step 4)

100.0 g of the compound represented by Chemical Formula 6 obtained in the step 3, 396.0 g of methanol, and 48.5 g of methylamine (9.8 M in methanol) were added to a new flask, and stirred for 30 minutes while adjusting the internal temperature to 10 to 15° C.

Thereafter, the internal temperature was cooled down to −10 to −5° C., and 4.8 g of sodium borohydride was dividedly added in a temperature range of −10 to −5° C., followed by stirring at −5 to 0° C. for 30 minutes.

Thereafter, 1,000 g of purified water was gradually added while maintaining an internal temperature of −5 to 15° C., and 902.0 g of ethyl acetate was added. Subsequently, the pH was adjusted to 6.7 to 7.3 using a 6N-aqueous hydrochloric acid solution while maintaining the internal temperature at 10 to 20° C.

Then, after stirring for 10 minutes, the mixture was allowed to stand for 30 minutes to separate the layers, and the organic layer was stored. 451.0 g of ethyl acetate was added to the resulting aqueous layer, stirred for 10 minutes, and then allowed to stand for 10 minutes. Thereafter, layer separation was performed, and the organic layer was combined with the organic layer obtained earlier, and the same re-extraction process was performed again.

Then, 600.0 g of aqueous sodium chloride solution (100.0 g of sodium chloride, 500.0 g of purified water) was added to the combined organic layer, stirred for 10 minutes, and allowed to stand for 10 minutes to separate the layers, followed by discarding the aqueous layer.

100.0 g of magnesium sulfate was added to the organic layer, stirred for 10 minutes while maintaining an internal temperature of 20 to 30° C., and then filtered under reduced pressure. The filtrate was washed with 270.6 g of ethyl acetate, and the filtrate was concentrated under reduced pressure at 38 to 42° C.

(Step 5)

90.2 g of ethyl acetate was added to the concentrated residue, stirred until a relatively uniform state, and 460.5 g of a 1.0M hydrochloric acid, ethyl acetate solution was added at a time at an internal temperature of 0 to 5° C. Then, the mixture was stirred at 0 to 5° C. for 1 hour or more to crystallize the compound represented by Chemical Formula 1-1.

The resulting crystals were filtered under reduced pressure, and the filtrate was washed with 90.2 g of ethyl acetate.

815.4 g of the filtrate and ethyl acetate were added to a new flask, cooled down to an internal temperature of 10 to 20° C., and stirred for 10 minutes. Thereafter, 976.3 g of aqueous sodium hydrogen carbonate solution (72.3 g of sodium hydrogen carbonate, 904.0 g of purified water) was added at an internal temperature of 10 to 20 °C, stirred for 10 minutes, and allowed to stand for 30 minutes to separate the layers, followed by storing the organic layer.

407.7 g of ethyl acetate was added to the aqueous layer, stirred for 10 minutes, and allowed to stand for 10 minutes to separate the layers. The organic layer was combined with the organic layer obtained earlier, and the aqueous layer was re-extracted again in the same procedure and combined with the organic layer.

90.4 g of magnesium sulfate was added to the organic layer, stirred at an internal temperature of 20 to 25° C. for 10 minutes, and then filtered under reduced pressure. The filtrate was washed with 244.6 g of ethyl acetate, and the filtrate was concentrated under reduced pressure at 38 to 42° C.

After 81.5 g of ethyl acetate was added to the concentrated residue and stirred, 368.4 g of a 1.0M hydrochloric acid, ethyl acetate solution was added at a time at an internal temperature of 0 to 5° C., followed by stirring at 0 to 5° C. for 4 hours or more to recrystallize.

The resulting crystals were filtered under reduced pressure, and the filtrate was washed with 81.5 g of ethyl acetate. The resulting filtrate was put in a dryer, vacuum-dried at a temperature of 20 to 30° C. for 12 hours, and further dried for 6 hours by heating to 38 to 42° C. to obtain 90.7 g of a compound represented by Chemical Formula 1-1 (yield: 80.2%).

$^1$H-NMR (500 MHZ, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

Comparative Example

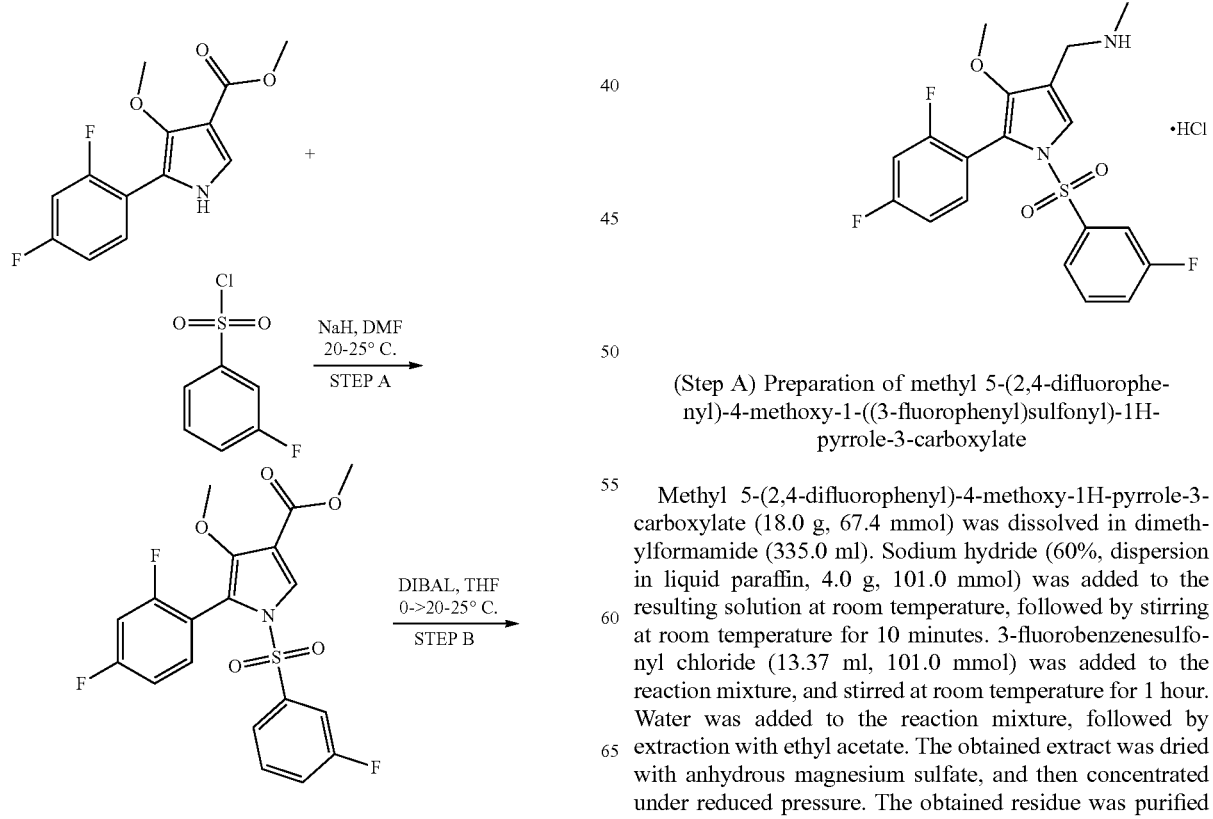

(Step A) Preparation of methyl 5-(2,4-difluorophenyl)-4-methoxy-1-((3-fluorophenyl)sulfonyl)-1H-pyrrole-3-carboxylate Methyl 5-(2,4-difluorophenyl)-4-methoxy-1H-pyrrole-3-carboxylate (18.0 g, 67.4 mmol) was dissolved in dimethylformamide (335.0 ml). Sodium hydride (60%, dispersion in liquid paraffin, 4.0 g, 101.0 mmol) was added to the resulting solution at room temperature, followed by stirring at room temperature for 10 minutes. 3-fluorobenzenesulfonyl chloride (13.37 ml, 101.0 mmol) was added to the reaction mixture, and stirred at room temperature for 1 hour. Water was added to the reaction mixture, followed by extraction with ethyl acetate. The obtained extract was dried with anhydrous magnesium sulfate, and then concentrated under reduced pressure. The obtained residue was purified by silica gel column chromatography (ethyl acetate:n-hexane=1:4(v/v)) to prepare 26.1 g of the title compound (Yield: 91.1%).

$^1$H-NMR (500 MHZ, CDCl$_3$): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)

(Step B) Preparation of 5-(2,4-difluorophenyl)-4-methoxy-1-((3-fluorophenyl)sulfonyl)-1H-pyrrole-3-carbaaldehyde Methyl 5-(2,4-difluorophenyl)-4-methoxy-1-((3-fluorophenyl)sulfonyl)-1H-pyrrole-3-carboxylate (26.0 g, 61.1 mmol) prepared in step A was dissolved in tetrahydrofuran (300.0 ml). Diisobutylaluminum hydride (1.0 M tetrahydrofuran solution, 183.4 ml, 183.4 mmol) was added to the obtained solution at 0° C., and stirred at room temperature for 1 hour. Thereafter, it was neutralized with a 1N hydrochloric acid solution and extracted with ethyl acetate. The obtained extract was dried with anhydrous magnesium sulfate, and then concentrated under reduced pressure.

After dissolving the obtained residue in dichloromethane (300.0 ml), celite (26.0 g) and pyridinium chlorochromate (39.5 g, 183.4 mmol) were added thereto. The reaction mixture was stirred at room temperature for 1 hour, filtered to remove a solid, and the obtained filtrate was concentrated under reduced pressure. The obtained residue was purified by silica gel column chromatography (ethyl acetate:n-hexane=1:2(v/v)) to prepare 17.2 g of the title compound (Yield: 70.9%).

$^1$H-NMR (500 MHZ, CDCl$_3$): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)

(Step C) Preparation of 1-(5-(2,4-difluorophenyl)-4-methoxy-1-((3-fluorophenyl) sulfonyl)-1H-pyrrol-3-yl)-N-methylmethanamine 5-(2,4-difluorophenyl)-4-methoxy-1-((3-fluorophenyl)sulfonyl)-1H-pyrrole-3-carbaaldehyde (17.0 g, 43.0 mmol) prepared in step B was dissolved in methanol (430.0 ml). Methylamine (9.8 M methanol solution, 87.8 ml, 860.0 mmol) was added to the obtained solution, followed by stirring at room temperature for 30 minutes. Sodium borohydride (16.3 g, 430.0 mmol) was added to the reaction mixture, followed by stirring at room temperature for 30 minutes. Water was added to the reaction mixture, followed by extraction with ethyl acetate. The obtained extract was dried with anhydrous magnesium sulfate, and then concentrated under reduced pressure. The obtained residue was purified by silica gel column chromatography (ethyl acetate: n-hexane=1:2(v/v)) to prepare 15.2 g of the title compound (Yield: 86.1%).

$^1$H-NMR (500 MHZ, CDCl$_3$): 7.39-7.35 (m, 1H), 7.26-7.20 (m, 2H), 7.15 (q, 1H), 7.06 (d, 1H), 6.87 (t, 1H), 6.78 (t, 1H), 3.60 (d, 2H), 3.44 (s, 3H), 2.45 (s, 3H)

(Step D) Preparation of 1-(5-(2,4-difluorophenyl)-1-((3-fluorophenyl)sulfonyl)-4-methoxy-1H-pyrrol-3-yl)-N-methylmethanamine hydrochloride After dissolving 1-(5-(2,4-difluorophenyl)-4-methoxy-1-((3-fluorophenyl)sulfonyl)-1H-pyrrol-3-yl)-N-methylmethanamine (15.0 g, 36.6 mmol) prepared in step C in ethyl acetate (36.6 ml), a hydrochloric acid solution (2.0 M diethyl ether solution, 36.6 ml, 73.1 mmol) was added thereto. The reaction mixture was stirred at room temperature for 1 hour, filtered, and dried under reduced pressure to prepare 15.1 g of the title compound (Yield: 92.5%).

Molecular Weight 446.87

$^1$H-NMR (500 MHZ, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

Comparison of Examples and Comparative Example

The yield, quality, etc. of the 4-methoxypyrrole derivatives obtained according to the respective manufacturing methods of Examples and Comparative Example were evaluated as follows, and are shown in Table 1 below.

The yield of 4-methoxy pyrrole derivatives: It was calculated by substituting the weight of 4-methoxy pyrrole derivatives (Chemical Formula 1) recovered after completion of the reaction and the weight of methyl 5-(2,4-difluorophenyl)-4-methoxy-1H-pyrrole-3-carboxylate (Chemical Formula 2) before the reaction into the following Formula 1.

[Formula 1]

The yield of 4-methoxy pyrrole derivatives (%)=100%*{number of moles of 4-methoxy pyrrole derivatives (Chemical Formula 1) recovered after completion of reaction}/{number of moles of methyl 5-(2,4-difluorophenyl)-4-methoxy-1H-pyrrole-3-carboxylate (Chemical Formula 2) before reaction}

The purity of 4-methoxy pyrrole derivatives and the content of related substance B: The purity of 4-methoxy pyrrole derivatives (Chemical Formula 1) recovered after completion of the reaction and the content of related substance B were measured using high performance liquid chromatography (HPLC, manufacturer: Waters, e2695 system).

Herein, the related substance B is 1-(5-(2,4-difluorophenyl)-4-methoxy-1H-pyrrol-3-yl)-N-methylmethanamine.

TABLE 1

|  | Comparative Example | Example 1 | Example 2 |
|---|---|---|---|
| Yield | 51.4% | 70.0% | 70.0% |
| Quality | Purity 99.5% or more | Purity 99.5% or more | Purity 99.5% or more |
|  | Related substance B 0.05% or less | Related substance B 0.23~0.26% | Related substance B 0.05% or less |

Referring to Table 1, it was confirmed that Examples not only improved the process efficiency compared to Comparative Example, but also improved the yield by about 1.4 times compared to Comparative Example.

When manufacturing the 4-methoxy pyrrole derivatives represented by Chemical Formula 1 using a 5 ton reaction facility according to Examples 1 and 2, it is possible to produce 167 kg, and thus it is inferred that the production volume increases by about three times compared to Comparative Example capable of producing 56 kg.

Further, according to Examples 1 and 2, industrial mass production is possible by a step-by-step crystallization process, and it is expected that the material cost per kg can be reduced by about 7 times compared to Comparative Example.

Specifically, in Examples and Comparative Example, the same starting material (i.e., compound represented by Chemical Formula 4) was used, and the same final material (i.e., 4-methoxy pyrrole derivatives represented by Chemical Formula 1) was prepared by performing the reaction in approximately four steps.

However, the major difference between Examples with respect to Comparative Example lies in the type of reductant used in step 2 of the 4-step reaction, and whether the steps 2 and 3 are configured in an in-situ manner.

Specifically, as the above Examples particularly used sodium borohydride as a reductant in step 2, and (2,2,6,6-tetramethylpiperidin-1-yl)oxyl as an oxidant in step 3, the use of hazardous reagents and environmental polluting reagents could be avoided. In addition, process convenience could be improved by configuring the step 3 in an in-situ manner using the concentrated residue of step 2 as it is.

On the other hand, the above Comparative Example used diisobutylaluminum hydride (DIBAL) which is a hazardous reagent and pyridinium chlorochromate which is an environmental polluting reagent as a reductant in step B corresponding to step 2 of Examples. Since these reagents were not easily removed, purification was performed through a silica column, and the process could not be configured in an in-situ manner.

In addition, the above Comparative Example used sodium hydride which is a hazardous reagent in step A corresponding to step 1 of Examples. On the other hand, the above Examples also have an advantage of not using such a material.

Therefore, the above Examples are meaningful in that they are useful for industrial mass production of 4-methoxypyrrole derivatives, because the process efficiency and the yield of the final material are improved compared to Comparative Example, and the use of hazardous reagents and environmental polluting reagents is avoided.

Meanwhile, the above Examples are only examples of the above-described embodiment, and they may control quality while improving the yield of the final material and the process efficiency.

In the above Example 2, a final material having a lower content of related substances compared to Example 1 was obtained. This is inferred to be a result of the following processes: the reaction temperature and drying temperature are raised to obtain a material having a lower moisture content (i.e., compound represented by Chemical Formula 4) in step 1; the stirring temperature is lowered and the stirring time is increased after adding methylamine to completely dissolve in step 4; and the reaction is quickly completed while raising the input temperature of 1.0M hydrochloric acid, ethyl acetate solution and the stirring temperature in step 5.

With reference to these Examples, it is possible to control the quality while improving the yield of the final material and the process efficiency by adjusting the process temperature and time of each step within the range of the above-described embodiment.

The invention claimed is:
1. A method for manufacturing 4-methoxypyrrole derivatives, comprising:
   1) a step of preparing a compound represented by the following Chemical Formula 4 by reacting a compound represented by the following Chemical Formula 2 with a compound represented by the following Chemical Formula 3;
   2) a step of preparing a compound represented by the following Chemical Formula 5 by reacting a compound represented by the following Chemical Formula 4 with sodium borohydride;
   3) a step of preparing a compound represented by the following Chemical Formula 6 by reacting a compound represented by the following Chemical Formula 5 with an oxidant; and
   4) a step of reacting a compound represented by the following Chemical Formula 6 with methylamine to produce an intermediate, and converting the intermediate to a compound represented by the following Chemical Formula 1 by adding a reductant:

[Chemical Formula 1]

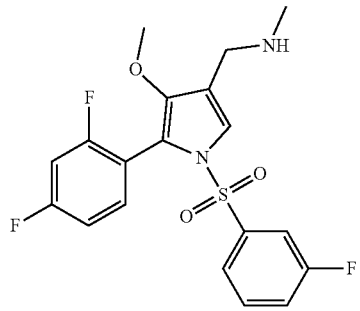

[Chemical Formula 2]

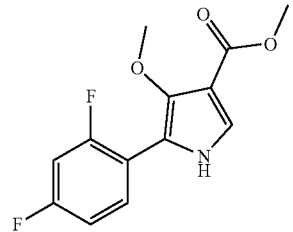

[Chemical Formula 3]

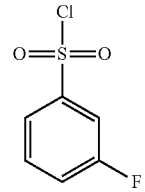

[Chemical Formula 4]

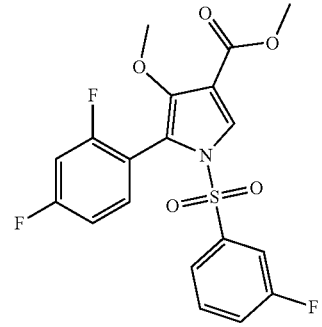

[Chemical Formula 5]

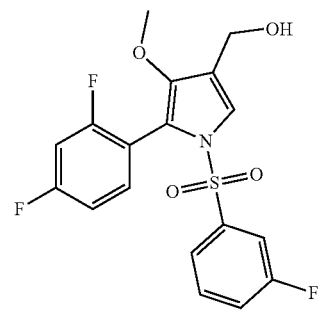

-continued

[Chemical Formula 6]

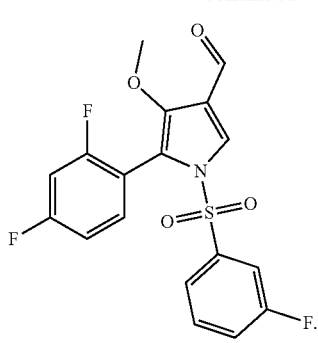

2. The method of claim 1, wherein the step 1 is performed in the presence of a base and 4-(dimethylamino)-pyridine.

3. The method of claim 2, wherein the base of the step 1 is N,N-diisopropylethylamine, triethylamine, diisopropylamine, diisopropylethylamine, potassium carbonate, potassium hydrogen carbonate, sodium carbonate, sodium hydrogen carbonate, sodium hydroxide, potassium hydroxide, lithium hydroxide, sodium methylate, potassium butyrate, cesium carbonate, or a mixture of two or more thereof.

4. The method of claim 1, wherein a molar ratio of the compound represented by the Chemical Formula 2 and the compound represented by the Chemical Formula 3 is 10:1 to 1:10 in the step 1.

5. The method of claim 1, wherein a reaction solvent of the step 1 is acetonitrile, tetrahydrofuran, methylene chloride, methanol, ethanol, propanol, iso-propanol, butanol, tert-butanol, or a mixture of two or more thereof.

6. The method of claim 1, wherein a reaction temperature in the step 1 is 10° C. to 35° C.

7. The method of claim 1, wherein the step 2 is performed in the presence of zinc chloride and dimethylaniline.

8. The method of claim 7, wherein the zinc chloride and the dimethylaniline are mixed to satisfy a molar ratio of the compound represented by the Chemical Formula 4 and the zinc chloride of 10:1 to 1:10, and a molar ratio of the compound represented by the Chemical Formula 4 and the dimethylaniline of 10:1 to 1:10 at the same time, and then used in the reaction of step 2.

9. The method of claim 1, wherein a reaction solvent of the step 2 is dimethylacetamide, tetrahydrofuran, dimethyl sulfoxide, toluene, methanol, ethanol, dichloromethane, or a mixture of two or more thereof.

10. The method of claim 1, wherein a reaction temperature in the step 2 is −15° C. to 80° C.

11. The method of claim 1, wherein the oxidation of step 3 is performed in the presence of
1) an oxidant selected from (diacetoxyiodo)benzene, iodine, iodobenzene dichloride, iodosylbenzene, and trichloroisocyanuric acid;
2) a catalyst selected from (2,2,6,6-tetramethylpiperidin-1-yl)oxyl, 4-acetamido-2,2,6,6-tetramethylpiperidine 1-oxyl, 4-hydroxy-2,2,6,6-tetramethylpiperidine 1-oxyl, 4-methacryloyloxy-2,2,6,6-tetramethylpiperidine-1-oxyl, 4-oxo-2,2,6,6-tetramethyl-1-piperidinyloxy, 4-amino-2,2,6,6-tetramethylpiperidin-1-oxyl, 4-carboxy-2,2,6,6-tetramethylpiperidine 1-oxyl, 4-hydroxy-2,2,6,6-tetramethylpiperidine 1-oxyl benzoate, 4-(2-iodoacetamido)-2,2,6,6-tetramethyl-1-piperidinyloxy, 4-maleimido-2,2,6,6-tetramethyl-1-piperidinyloxy, 4-isothiocyanato-2,2,6,6-tetramethylpiperidine 1-oxyl, 4-methoxy-2,2,6,6-tetramethyl-1-piperidinyloxy, and 4-phosphonooxy-2,2,6,6-tetramethyl-1-piperidinyloxy; or
a mixture of one oxidant selected from 1) and one catalyst selected from 2).

12. The method of claim 11,
wherein the oxidation of the step 3 is performed in the presence of a mixture of the (diacetoxyiodo)benzene and the (2,2,6,6-tetramethylpiperidin-1-yl)oxyl, and
the (diacetoxyiodo)benzene and the (2,2,6,6-tetramethylpiperidin-1-yl)oxyl are mixed to satisfy a molar ratio of the compound represented by the Chemical Formula 5 and the (diacetoxyiodo)benzene of 10:1 to 1:10, and a molar ratio of the compound represented by the Chemical Formula 5 and the (2,2,6,6-tetramethylpiperidin-1-yl)oxyl of 10:1 to 1:10 at the same time.

13. The method of claim 1, wherein a reaction solvent of the step 3 is dichloromethane, dichloroethane, acetonitrile, ethyl acetate, methanol, toluene, dimethylformamide, dimethyl sulfoxide, tetrahydrofuran, or a mixture of two or more thereof.

14. The method of claim 1, wherein a reaction temperature in the step 3 is 10° C. to 40° C.

15. The method of claim 1, wherein a reaction solvent of the step 4 is methanol, ethanol, isopropanol, dichloromethane, dichloroethane, tetrahydrofuran, ethyl acetate, dimethyl ether, acetonitrile, or a mixture of two or more thereof.

16. The method of claim 1, wherein the reaction of the compound represented by the Chemical Formula 6 and the methylamine is performed at a reaction temperature of 10° ° C. to 30° ° C. in the step 4.

17. The method of claim 1, wherein the reductant of the step 4 is sodium borohydride, sodium cyanoborohydride, sodium triacetoxyborohydride, or a mixture of two or more thereof.

18. The method of claim 1, wherein the reaction of the reductant and the intermediate is performed at a reaction temperature of −5° C. to 10° C. in the step 4.

19. The method of claim 1, wherein a molar ratio of the compound represented by the Chemical Formula 6 and the methylamine is 10:1 to 1:10, and a molar ratio of the compound represented by the Chemical Formula 6 and the reductant is 10:1 to 1:10 in the step 4.

20. The method of claim 1, further comprising a step preparing an acidic salt represented by the following Chemical Formula 1-1 by adding an acid to the compound represented by the Chemical Formula 1, after the step 4:

[Chemical Formula 1-1]

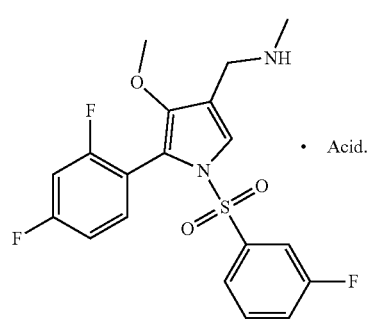

· Acid.

21. The method of claim 20, wherein the step after step 4 comprises a step of crystallizing the acidic salt represented by the Chemical Formula 1-1 by supplying an organic solvent to the compound represented by the Chemical Formula 1 and then supplying an acid or a mixed solution thereof with an organic solvent.

22. The method of claim 21, wherein the crystallization temperature is −15° C. to 20° C.

* * * * *

UNITED STATES PATENT AND TRADEMARK OFFICE
CERTIFICATE OF CORRECTION

| | | |
|---|---|---|
| PATENT NO. | : 12,110,271 B2 | Page 1 of 1 |
| APPLICATION NO. | : 17/273390 | |
| DATED | : October 8, 2024 | |
| INVENTOR(S) | : Jeong-Taek Shin et al. | |

It is certified that error appears in the above-identified patent and that said Letters Patent is hereby corrected as shown below:

In the Claims

At Column 28, Lines 30-31, "10° ° C. to 30° ° C." should be -- 10° C. to 30° C. --.

Signed and Sealed this
Eleventh Day of March, 2025

Coke Morgan Stewart
*Acting Director of the United States Patent and Trademark Office*